United States Patent [19]
Knutsson et al.

[11] Patent Number: 4,783,273
[45] Date of Patent: Nov. 8, 1988

[54] METHOD AND APPARATUS FOR SUPPLYING CONCENTRATE FOR USE IN MEDICAL TREATMENTS

[75] Inventors: Stefan L. Knutsson, Bjarred, Sweden; Stanley Shaldon, Montpellier, France

[73] Assignee: Gambro AB, Sweden

[21] Appl. No.: 133,995

[22] Filed: Dec. 17, 1987

[30] Foreign Application Priority Data

Jan. 29, 1987 [SE] Sweden .................................. 8700344

[51] Int. Cl.$^4$ .............................................. B01D 13/00
[52] U.S. Cl. ..................................... 210/798; 210/108; 210/195.2; 210/257.2; 210/258; 210/321.3; 210/433.2; 210/927; 210/321.72
[58] Field of Search ............................... 210/644–648, 210/649–652, 791, 797, 798, 106, 108, 194, 195.1, 195.2, 258, 257.2, 321.1, 321.2, 321.3, 333.01, 409, 411, 416.1, 425, 427, 433.2

[56] References Cited

U.S. PATENT DOCUMENTS

| | | | |
|---|---|---|---|
| 4,338,190 | 7/1982 | Kraus et al. | 210/195.2 |
| 4,366,051 | 12/1982 | Fischer | 210/188 |
| 4,530,759 | 7/1985 | Schäl | 210/927 |
| 4,683,053 | 7/1987 | Polaschegg | 210/929 |
| 4,695,385 | 9/1987 | Boag | 210/746 |

Primary Examiner—Frank Sever
Attorney, Agent, or Firm—Lerner, David, Littenberg, Krumholz & Mentlik

[57] ABSTRACT

Apparatus for the supply of concentrate for use in medical treatment processes is disclosed, including a concentrate filter including a membrane, an inlet conduit for supplying concentrate to the inlet side of the concentrate filter during normal use and for supplying cleaning fluid to the inlet side of the concentrate filter during cleaning, an outlet conduit for withdrawing the filtered concentrate or a portion of the cleaning fluid from the outlet side of the concentrate filter, and a cleaning fluid withdrawal conduit connected to the inlet side of the concentrate filter and including a valve so that it can be closed during normal use of the concentrate filter and opened during cleaning of the concentrate filter in order to flush a portion of the cleaning fluid through the concentrate filter. Methods for supplying concentrate to be used for medical treatment purposes are also disclosed.

25 Claims, 2 Drawing Sheets

METHOD AND APPARATUS FOR SUPPLYING CONCENTRATE FOR USE IN MEDICAL TREATMENTS

FIELD OF THE INVENTION

The present invention relates to methods and apparatus for the preparation of fluids intended to be used for medical treatment purposes. More particularly, the present invention relates to methods and apparatus for mixing water with at least one such concentrate which is filtered prior to mixing. Still more particularly, the present invention relates to methods and apparatus for supplying concentrate to be used in medical treatments, and for intermittently cleaning the apparatus used therefor.

BACKGROUND OF THE INVENTION

Systems for the preparation of fluids intended to be used for medical treatment purposes are particularly useful for the preparation of dialysis fluid in connection with hemodialysis. However, with minor modifications such systems can also be used for the preparation of replacement fluids in connection with hemofiltration or hemodiafiltration. Those versed in this art will immediately recognize that these systems can thus be used in connection with other methods of treatment in which the mixing of pure water with at least one concentrate is required in order to produce a solution which is preferably entirely bacteria-free and substantially pyrogen-free.

In conventional hemodialysis blood is conducted to one side of a membrane in the dialyzer, and at the same time dialysis fluid is conducted to the opposite side of that membrane. Poisons which one wishes to remove from the blood are in such a case passed from the blood to the dialysis fluid by means of diffusion through the membrane. Under normal circumstances, a certain amount of fluid, primarily water, is at the same time withdrawn through ultrafiltration so that there is some degree of lowering of the patient's weight effected thereby.

Hemodiafiltration differs from hemodialysis most particularly in that a more permeable filter is used and therefore greater ultrafiltration is obtained. This, in turn, makes it necessary for a portion of the ultrafiltrate to be replaced by replacement fluid. In hemofiltration no dialysis fluid is utilized. Instead, with the assistance of a filter, a large quantity of ultrafiltrate is withdrawn, and this must be at least partly replaced by a corresponding quantity of replacement fluid.

Each of these hemodialysis, hemodiafiltration, and hemofiltration processes requires different types of control arrangements to be utilized, but in each of them at least one concentrate is generally mixed with pure water. Certain of these concentrates are of a type which prevent bacterial growth. In that case there are no major problems and the concentrate can be directly mixed with the water. Other concentrates, however, such as those based on bicarbonate, favor bacteria growth and therefore must be filtered, i.e., before they are mixed with the water. The filters used for these purposes are designed for low percolation, which renders the sterilization and/or disinfection required between respective treatments somewhat difficult.

SUMMARY OF THE INVENTION

In accordance with the present invention, the above-mentioned difficulties in connection with the sterilization and/or disinfection of both the concentrate filter and the overall system itself has not been provided. These and other problems have now been resolved by utilization of a system in which, for purposes of disinfection and/or sterilization (i.e., cleaning) the filter is adapted to be flushed through on its inlet side with a cleaning fluid, a portion of which is utilized for withdrawal through the filtering material on the outlet side of the filter normally used for the filtered concentrate. By means of this flushing technique, this can be carried out irrespective of flows which normally occur through the filter, and at the same time the filtrate side can also be effectively cleaned or treated.

The present invention is therefore intended to be applied in connection with both sterilization and disinfection. However, for the sake of simplicity in the following detailed description it will be described in connection with sterilization.

In accordance with the apparatus of the present invention, the apparatus includes a concentrate filter which includes an inlet side and an outlet side separated by a membrane, inlet conduit means for supplying concentrate to the inlet side of the concentrate filter during normal use of the concentrate filter and for supplying a cleaning fluid to the inlet side of the concentrate filter during cleaning of the concentrate filter, outlet conduit means for withdrawing the filtered concentrate from the outlet side of the concentrate filter during normal use of the concentrate filter and for withdrawing a first position of the cleaning fluid from the outlet side of the concentrate filter during cleaning of the concentrate filter, and cleaning fluid withdrawal means connected to the inlet side of the concentrate filter and including valve means so that the cleaning fluid withdrawal means can be closed during normal use of the concentrate filter and opened in order to flush a second portion of the cleaning fluid through the concentrate filter during cleaning of the concentrate filter.

In accordance with one embodiment of the apparatus of the present invention, drain means are provided for disposal of the second portion of the cleaning fluid passing through the cleaning fluid withdrawal means.

In accordance with another embodiment of the apparatus of the present invention, the cleaning fluid withdrawal means includes pressure control valve means for controlling the pressure within the cleaning fluid withdrawal means.

In accordance with one embodiment of the apparatus of the present invention, the cleaning fluid withdrawal means includes pressure control valve means for controlling the pressure within the cleaning fluid withdrawal means. In another embodiment the outlet conduit means includes suction pump means for withdrawing the filtered concentrate from the outlet side of the concentrate filter during normal use of the concentrate filter and for withdrawing the cleaning fluid from the outlet side of the concentrate filter during cleaning of the concentrate filter.

In a preferred embodiment this apparatus includes first concentrate supply means for supplying the concentrate to the inlet conduit means during normal use of the concentrate filter, medical treatment conduit means for supplying the filtered concentrate withdrawn from the outlet side of the concentrate filter for medical treatment purposes during normal use of the concentrate filter and for carrying the first portion of the cleaning fluid withdrawn from the outlet side of the concentrate filter during cleaning of the concentrate filter, additional concentrate supply means for supplying additional concentrate to be used for the medical treatment purposes, including additional concentrate conduit means for supplying the additional concentrate to the medical treatment conduit means, in which the suction pump means in the outlet conduit means comprises a first suction pump means, and including a second suction pump means in the additional concentrate supply means for supplying the additional concentrate to the medical treatment conduit means during normal use of the concentrate filter, disconnect means for disconnecting the first and second concentrate supply means from the inlet conduit means and the additional concentrate conduit means, respectively, and common cleaning fluid supply means for suplying the cleaning fluid to the inlet conduit means and the additional concentrate conduit means so that the cleaning fluid can be supplied both to the inlet side of the concentrate filter and to the additional concentrate conduit means during cleaning of the concentrate filter.

In accordance with another embodiment of this apparatus, branch outlet conduit means are also provided connected to the outlet conduit means for withdrawing at least a portion of the first portion of the cleaning fluid withdrawn from the outlet side of the concentrate filter during cleaning of the concentrate filter, the branch outlet conduit means including drain means for disposal of said at least a portion of the first portion of the cleaning fluid.

In accordance with a preferred embodiment of this apparatus of the present invention, a branch outlet conduit means is located between the concentrate filter and the suction pump means. In another embodiment of the branch outlet conduit means includes pressure control valve means for controlling the pressure within the branch outlet conduit means.

In accordance with a preferred embodiment of the apparatus of the present invention, the apparatus includes a water filter, including an inlet side and an outlet side separated by a membrane, water inlet conduit means for supplying water to the inlet side of the water filter during normal use of the water filter and for supplying cleaning fluid to the inlet side of the water filter during cleaning of the water filter, water outlet conduit means for withdrawing the filtered water from the outlet side of the water filter during normal use of the water filter and for withdrawing at least a portion of the cleaning fluid from the outlet side of the water filter during cleaning of the water filter, unfiltered cleaning fluid withdrawal means connected to the inlet side of the water filter, and including valve means whereby the unfiltered cleaning fluid withdrawal means can be closed during normal use of the water filter and opened in order to fluch a second portion of the cleaning fluid through the water filter during cleaning of the water filter, and water fluid connection means for connecting the water outlet conduit means to the inlet conduit means for supplying the cleaning fluid to the inlet side of the concentrate filter during cleaning of the concentrate filter.

In a preferred embodiment this apparatus includes supply duct means connected to the water inlet conduit means for supplying cleaning fluid to the water inlet conduit means during cleaning of the water filter.

In accordance with the method of the present invention, these above objects have been accomplished by a method which includes supplying concentrate to the inlet side of a concentrate filter, withdrawing the filtered concentrate from the outlet side of the concentrate filter, intermittently terminating the supply of the concentrate to the inlet side of the concentrate filter and supplying cleaning fluid to the inlet side of the concentrate filter so as to clean the concentrate filter, withdrawing a first portion of the cleaning fluid from the outlet side of the concentrate filter, and withdrawing a second portion of the cleaning fluid from the inlet side of the concentrate filter so as to simultaneously flush the inlet side and the outlet side of the concentrate filter with the cleaning fluid during cleaning of the concentrate filter.

In accordance with one embodiment of the method of the present invention, the method includes disposing of the second portion of the cleaning fluid withdrawn from the inlet side of the concentrate filter.

In accordance with another embodiment of the method of the present invention, the method includes controlling the pressure of the second portion of the cleaning fluid withdrawn from the inlet side of the concentrate filter. In another embodiment, the method includes pumping the filtered concentrate withdrawn from the outlet side of the concentrate filter and pumping the first portion of the cleaning fluid intermittently withdrawn from the outlet side of the concentrate filter.

In accordance with a preferred embodiment of the method of the present invention in which the concentrate supplied to the inlet side of the concentrate filter comprises a first concentrate portion, the method includes supplying the filtered first concentrate portion withdrawn from the outlet side of the concentrate filter to a primary supply conduit for the medical treatment purposes, supplying a second concentrate portion to the primary supply conduit, pumping the filtered first concentrate portion to the primary supply conduit, pumping the second concentrate portion to the primary supply conduit, and intermittently disconnecting the supply of the first and second concentrate portions and supplying the cleaning fluid to both the inlet side of the concentrate filter and the primary supply conduit during cleaning of the concentrate filter.

In accordance with another embodiment of the method of the present invention, the method includes withdrawing at least a portion of the first portion of the cleaning fluid withdrawn from the outlet side of the concentrate filter and disposing of that at least a portion of the first portion of the cleaning fluid.

In a preferred embodiment this method includes controlling the pressure in the at least a portion of the first portion of the cleaning fluid withdrawn from the outlet side of the concentrate filter.

In another embodiment the method includes controlling the pressure in that at least a portion of the first portion of the cleaing fluid withdrawn from the outlet side of the concentrate filter and controlling the pressure in the second portion of the cleaning fluid withdrawn from the inlet side of the concentrate filter.

In accordance with a preferred embodiment of the method of the present invention, the method includes supplying water to the inlet side of a water filter, withdrawing the filtered water from the outlet side of the water filter, intermittently supplying cleaning fluid to the inlet side of the water filter so as to clean the water filter, withdrawing a first portion of the cleaning fluid from the outlet side of the water filter, withdrawing a second portion of the cleaning fluid from the inlet side of the water filter, so as to simultaneously flush the inlet side and the outlet side of the water filter with cleaning fluid during cleaning of the water filter, supplying the filtered water withdrawn from the outlet side of the water filter to the primary supply conduit for the medical treatment purposes, and intermittently supplying at least a portion of the cleaning fluid withdrawn from the outlet side of the water filter to the inlet side of the concentrate filter so as to clean the concentrate filter.

On an overall basis, the system is preferably arranged so that a cleaning fluid can be supplied to the inlet of the filter normally used for the supply of concentrate, and it can be discharged to a drain by a connection which preferably includes a pressure control valve. As a result of the use of this apparatus, appropriate thorough flushing of the inlet side of the filter can be achieved while at the same time a portion of the fluid can be forced through the filtering material or membrane to obtain effective sterilization on the filtrate side of the filter. Furthermore, at least a portion of the fluid which is forced through the filtering material is preferably also passed through the system with the help of a suction pump, namely the suction pump which is normally used for the suction of concentrate through the same ducts.

As is further outlined above, this system can also be appropriately utilized in installations which include two sources of concentrate which are connected to the overall system by means of two connecting ducts, at least one of which is provided with a filter of the above-discussed type, and each of which is preferably connected to a suction pump. In this manner a simple changeover from normal treatment to sterilization can be achieved in this case if the two sources of concentrate are adapted so that they can be disconnected with the two connecting ducts then being joined together in an appropriate manner.

As is also outlined above, in order to improve the percolation of the filtrate on the filtrate side of the filter a branch duct connected to a drain can be adapted in order to originate from a point in the associated connecting duct between the outlet for the filtered concentrate and the suction pump arranged in that duct.

In order to control the flow through this branch duct a pressure control valve is preferably arranged therein. By utilizing this valve and the aforementioned pressure control valve appropriate flow rates can be achieved on the inlet side of the filter as well as on the filtrate side thereof. The main principle involved is that the pressure control valve between that connection and the outlet can be set to a higher resistance pressure than the pressure control valve in the branch duct. In view of this pressure difference a suitable amount of sterilizing fluid can thus be forced through the filtering material.

As is also noted above, the water which is utilized must also be filtered prior to mixing, preferably by means of a water filter which includes a water inlet connected to a source of water and an outlet for filtered water, as well as an outlet for non-filtered water connected to a drain. In this system the outlet for the filtered water is again arranged so that it can be connected on the one hand to a point for mixing the concentrate and on the other hand directly to the concentrate filter. The supply duct for the sterilizing or cleaning fluid may in this case be arranged prior to the inlet of the water filter. The direct connection between the water filter and the concentrate filter is used only in connection with sterilization and/or subsequent rinsing thereof. In view thereof a shut-off valve must be provided between the two filters.

BRIEF DESCRIPTION OF THE DRAWINGS

The present invention may be more fully appreciated with reference to the following detailed description, which in turn refers to the following drawings in which.

DETAILED DESCRIPTION

Figure 1:
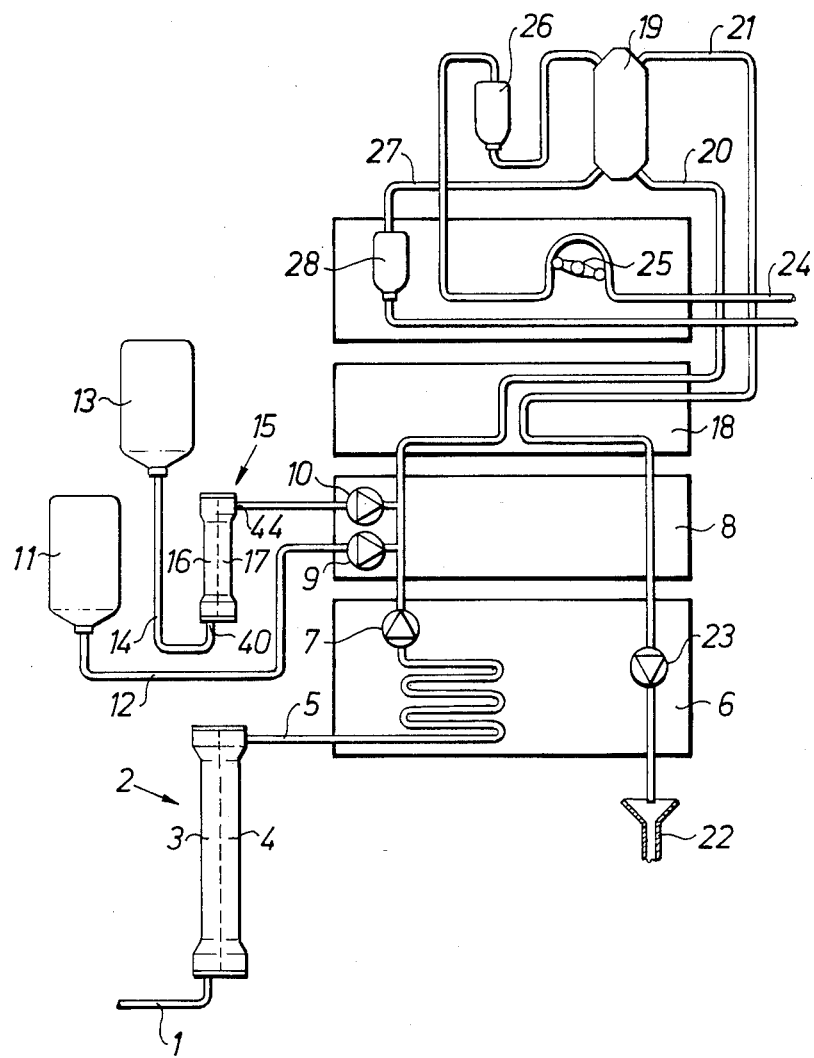
FIG. 1 is a schematic representation of the apparatus and method of the present invention utilizing a hemodialysis system.
Figure 2:
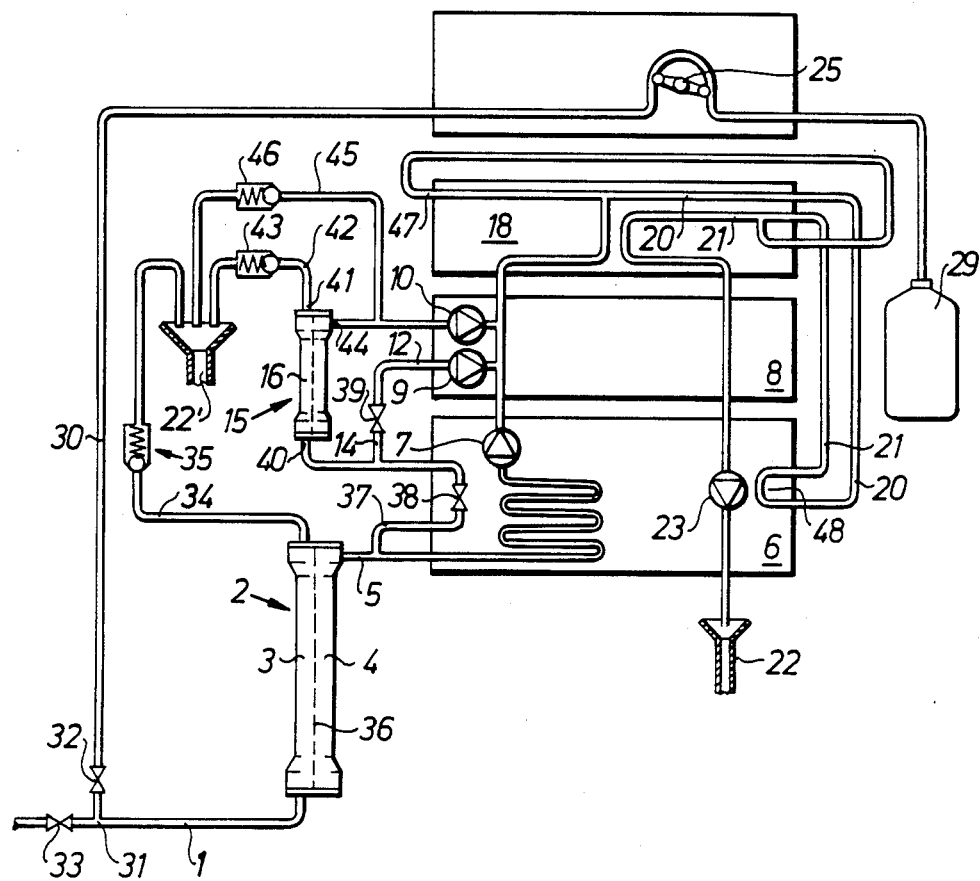
FIG. 2 is a schematic representation of the system shown in FIG. 1 arranged for chemical sterilization and/or subsequent rinsing thereof.

Referring to the Figures, in which like numerals refer to like portions thereof, FIG. 1 primarily shows those components of the system which are necessary for actual dialysis treatment. Those additional components which are used for sterilization and/or rinsing, i.e., for cleaning, are shown in FIG. 2. In both of these Figures components which are of less significance in understanding the present invention, such as conventional pressure gauges, conductivity meters, temperature measuring instruments, etc., have not been included therein.

Referring first to FIG. 1, in the system shown therein water is supplied from a water source which is not shown in FIG. 1, by means of duct 1, into a water filter 2 which is divided into an inlet side 3 and an outlet or filtrate side 4. The filtered water then passes through a duct 5 into a conventional dialysis monitor 6, which can include the necessary means for treatment of the water, e.g. heating means, as well as means for checking temperature and pressure. This monitor can, for example, be designed in accordance with U.S. Pat. No. 4,158,034, the disclosure of which is incorporated herein by reference thereto.

With the assistance of a pump 7 the water is then conducted to a mixing monitor 8, which in the case shown in FIG. 1 comprises two concentrate pumps, 9 and 10, respectively. During normal dialysis treatment the concentrate pump 9 draws concentrate from a source 11 through a duct 12. In the same manner, the pump 10 draws concentrate from a source 13 through a duct 14 and a filter 15. The filter 15 can also be said to be divided into an inlet side 16 and an outlet or filtrate side 17, respectively. After mixing of the concentrate with the water, the conductivity of the mixture is checked in a conductivity meter, which is not shown in FIG. 1, and which may be located in the conventional dialysis monitor 6 or in the mixing monitor 8. Further details regarding this mixing may be found in EP No. 0 022 922 B1.

From the mixing monitor 8 of the dialysis solution is then passed through flow control monitor 18 to a dialyzer 19, by means of a duct 20. The dialysate which is obtained in the dialyzer 19 is returned again through the flow control monitor 18 and dialysis monitor 6, to a drain 22. This is done with the help of a suction pump 23 in order to maintain an appropriate low pressure in dialyzer 19. Flow control monitor 18 is described in more detail, for example, in U.S. Pat. No. 4,585,552, which is also incorporated herein by reference thereto.

Blood is withdrawn from a patient (not shown) through a duct 24 and is pumped, with the assistance of pump 25, through a drip chamber 26, to dialyzer 19, and from here through a duct 27 with a drip chamber 28 back to the patient.

The system desribed above can be said to be largely conventional, and difficulties may therefore arise in connection with sterilization of the concentrate filter 15. However, the system can be modified in accordance with the present invention in the manner shown in FIG. 2, in which the same reference designations have been used as in FIG. 1 for those components which correspond to each other therein. The system is thus shown in this case as modified for chemical sterilization and/or subsequent rinsing, i.e., for cleaning. As can be seen, the dialyzer 19 and the associated blood ducts have been eliminated. Instead, the blood pump 25 is now used for the supply of a sterilizing fluid, e.g. formaldehyde, from a source 29. This fluid is passed through a duct 30 to a point 31 in the water inlet duct. Reference numeral 32 is intended to schematically designate either a shut-off cock or a disconnecting device. In the same manner, reference numeral 33 is intended to designate a shut-off cock in the water duct 1. With the cock 32 open and the cock 33 closed sterilizing fluid can thus be introduced into the inlet side 3 of the water filter 2, from which a portion thereof is conducted through a duct 34 with a check valve 35 to a drain 22', which may in principle be identical to that designated 22. Alternatively, concentrated sterilizing fluid can be passed from the source 29 to the point 31 where it is mixed with an appropriate amount of water. In view of the presence of check valve 35, a portion of the sterilizing fluid is forced to pass through the filtering material, which normally consists of one or more membranes 36, generally in the form of flat films or hollow fibers. This percolation is facilitated by pump 7 provided in the dialysis monitor 6. A part of the sterilizing fluid, however, is conducted through duct 37 and valve 38 directly to the concentrate filter 15. Just prior to the latter, however, a further partial stream is diverted through the connecting ducts 12 and 14, which are joined together at 39. This partial stream is drawn by means of pump 9 into the main stream, i.e., the primary conduit for medical treatment purposes. The sterilizing fluid flows into the filter 15 by means of the normal concentrate inlet 40 and flushes through the inlet side 16 of this filter. It leaves the filter through a connection 41 and a duct 42, with a pressure control valve 43, to ultimately flow out into drain 22'. By means of the pressure control valve 43, however, a portion of the sterilizing fluid is pressed through the filtering material to the outlet 44, which again is normally used for the filtered concentrate. The fluid flowing out through this outlet is again divided into two partial streams, namely one to the main duct by means of pump 10, and a second stream to the drain 22' by means of a branch duct 45 with a pressure control valve 46.

In order to achieve an appropriate division of flow between ducts 42 and 45, the pressure control valve 43 must be set, or be settable, to a higher resistance pressure than the pressure control valve 46. By way of example, it can be said that at a pressure of 0.5–1.0 bar in the duct 5 it has been found appropriate to set the valve 43 to a counterpressure of approximately 200 mm Hg and the valve 46 to a counterpressure of approximately 100 mm Hg. At these pressures the valves 43 and 46 are automatically shut during normal operation.

From the pumps 7, 9 and 10 the sterilizing fluid then flows into the flow control monitor 18, where it divides into a branch duct 47 and the duct 20 which normally leads to the dialyzer. The branch duct 47 is intended to allow the system shown in the Figures to be further modified, so that it can also be used for hemofiltration and hemodiafiltration, respectively. The way in which this is done is described in more detail in Swedish patent application No. 86.03746-2.

Duct 20 has been disconnected from the dialyzer, and is instead connected to a so-called bypass arrangement 48. The same applies to duct 21 which normally leads away from the dialyzer. The manner in which this bypass arrangement functions is described, for example, in U.S. Pat. No. 4,122,010. From the bypass arrangement the sterilizing fluid is conducted through duct 21, flow control monitor 18, and dialysis monitor 6, with its pump 23, to the drain 22.

With regard to filters 2 and 15, it should finally be added that they must be bacteria-tight. By this it is meant that they must normally allow not more than one bacterium per million inflowing bacteria to pass therethrough. Moreover, pyrogens must also be separated to a high degree. It is normally required in this respect that they must not allow more than one pyrogen particle per 10,000 inflowing particles of this kind to pass therethrough.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. Apparatus for the supply of concentrate to be used for medical treatment purposes comprising means for enabling substantially easy sterilization and/or disinfection of low percolation filters when and/or where said concentrate favors bacterial growth, including, a concentrate filter, said concentrate filter including an inlet side and an outlet side separated by membrane means, inlet conduit means for supplying said concentrate to said inlet side of said concentrate filter during normal use of said concentrate filter and for supplying a cleaning fluid to said inlet side of said concentrate filter during cleaning of said concentrate filter, outlet conduit means for withdrawing said filtered concentrate from said outlet side of said concentrate filter during normal use of said concentrate filter and for withdrawing a first portion of said cleaning fluid from said outlet said of said concentrate filter during cleaning of said concentrate filter, and cleaning fluid withdrawal means connected to said inlet side of said concentrate filter, said cleaning fluid withdrawal means including valve means selected to enable said cleaning fluid withdrawal means to be closed during normal use of said concentrate filter and opened in order to flush a second portion of cleaning fluid through said concentrate filter during cleaning of said concentrate filter.

2. The apparatus of claim 1 including drain means for disposal of said second portion of said cleaning fluid passing through said cleaning fluid withdrawal means.

3. The apparatus of claim 1 wherein said cleaning fluid withdrawal means includes pressure control valve means for controlling the pressure within said cleaning fluid withdrawal means.

4. The apparatus of claim 1 wherein said cleaning fluid withdrawal means includes pressure control valve means for controlling the pressure within said cleaning fluid withdrawal means.

5. The apparatus of claim 1 wherein said outlet conduit means includes suction pump means for withdrawing said filtered concentrate from said outlet side of said concentrate filter during normal use of said concentrate filter and for withdrawing said cleaning fluid from said outlet side of said concentrate filter during cleaning of said concentrate filter.

6. The apparatus of claim 5 including first concentrate supply means for supplying said concentrate to said inlet conduit means during normal use of said concentrate filter, medical treatment conduit means for supplying said filtered concentrate withdrawn from said outlet side of said concentrate filter for said medical treatment purposes during normal use of said concentrate filter and for carrying said first portion of said cleaning fluid withdrawn from said outlet side of said concentrate filter during cleaning of said concentrate filter, additional concentrate supply means for supplying additional concentrate to be used for said medical treatment purposes, said additional concentrate supply means including additional concentrate conduit means for supplying said additional concentrate to said medical treatment conduit means, said suction pump means in said outlet conduit means comprising a first suction pump means, and including a second suction pump means in said additional concentrate supply means for supplying said additional concentrate to said medical treatment conduit means during normal use of said concentrate filter, disconnect means for disconnecting said first and second concentrate supply means from said inlet conduit means and said additional concentrate conduit means, respectively, and common cleaning fluid supply means for supplying said cleaning fluid to said inlet conduit means and said additional concentrate conduit means whereby said cleaning fluid can be supplied both to said inlet side of said concentrate filter and to said additional concentrate conduit means during cleaning of said concentrate filter.

7. The apparatus of claim 5 including branch outlet conduit means connected to said outlet conduit means for withdrawing at least a portion of said first portion of said cleaning fluid withdrawn from said outlet side of said concentrate filter during cleaning of said concentrate filter, said branch outlet conduit means including drain means for disposal of said at least a portion of said first portion of said cleaning fluid.

8. The apparatus of claim 7 wherein said branch outlet conduit means is located between said concentrate filter and said suction pump means.

9. The apparatus of claim 7 wherein said branch outlet conduit means includes pressure control valve means for controlling the pressure within said branch outlet conduit means.

10. The apparatus of claim 7 wherein said cleaning fluid withdrawal means includes first pressure control valve means for controlling the pressure within said cleaning fluid withdrawal means, and wherein said branch outlet conduit means includes second pressure control valve means for controlling the pressure within said branch outlet conduit means.

11. The apparatus of claim 10 wherein said first pressure control valve means is set at a higher pressure than said second pressure control valve means.

12. The apparatus of claim 1 including a water filter, said water filter including an inlet side and an outlet side separated by membrane means, water inlet conduit means for supplying said water to said inlet side of said water filter during normal use of said water filter and for supplying cleaning fluid to said inlet side of said water filter during cleaning of said water filter, water outlet conduit means for withdrawing said filtered water from said outlet side of said water filter during normal use of said water filter and for withdrawing at least a portion of said cleaning fluid from said outlet side of said water filter during cleaning of said water filter, unfiltered cleaning fluid withdrawal means connected to said inlet side of said water filter, said unfiltered cleaning filter withdrawal means including valve means whereby said unfiltered cleaning fluid withdrawal means may be closed during normal use of said water filter and opened in order to flush a second portion of said cleaning fluid through said water filter during cleaning of said water filter, and water fluid connection means for connecting said water outlet conduit means to said inlet conduit means for supplying said cleaning fluid to said inlet side of said concentrate filter during cleaning of said concentrate filter.

13. The apparatus of claim 12 including supply duct means connected to said water inlet conduit means for supplying cleaning fluid to said water inlet conduit means during cleaning of said water filter.

14. The apparatus of claim 13 wherein said water outlet conduit means includes shut-off valve means.

15. The apparatus of claim 14 wherein said shut-off valve means is located between said water filter and said concentrate filter.

16. A method for supplying concentrate to be used for medical treatment purposes comprising enabling easy sterilization and/or disinfection of low percolation filters when and/or where aid concentrate favors bacterial growth, by, supplying said concentrate to the inlet side of a concentrate filter, withdrawing said filtered concentrate from the outlet side of said concentrate filter, intermittently terminating the supply of said concentrate to said inlet side of said concentrate filter and supplying cleaning fluid to said inlet side of said concentrate filter so as to clean said concentrate filter, withdrawing a first portion of said cleaning fluid from said outlet side of said concentrate filter, and withdrawing a second portion of said cleaning fluid from said inlet side of said concentrate filter so as to simultaneously flush said inlet side and said outlet side of said concentrate filter with said cleaning fluid during said cleaning of said concentrate filter.

17. The method of claim 16 including disposing of said second portion of said cleaning fluid withdrawn from said inlet side of said concentrate filter.

18. The method of claim 16 including controlling the pressure of said second portion of said cleaning fluid withdrawn from said inlet side of said concentrate filter.

19. The method of claim 16 including pumping said filtered concentrate withdrawn from said outlet side of said concentrate filter, and pumping said first portion of said cleaning fluid intermittently withdrawn from said outlet side of said concentrate filter.

20. The method of claim 16 wherein said concentrate supplied to said inlet side of said concentrate filter comprises a first concentrate portion, and including supplying said filtered first concentrate portion withdrawn from said outlet side of said concentrate filter to a primary supply conduit for said medical treatment process, supplying a second concentrate portion to said primary supply conduit, pumping said filtered first concentrate portion to said primary supply conduit, pumping said second concentrate portion to said primary supply conduit, and intermittently disconnecting said supply of said first and said second concentrate portions and supplying said cleaning fluid to both said inlet side of said concentrate filter and said primary supply conduit during cleaning of said concentrate filter.

21. The method of claim 16 including withdrawing at least a portion of said first portion of said cleaning fluid withdrawn from said outlet side of said concentrate filter, and disposing of said at least a portion of said first portion of said cleaning fluid.

22. The method of claim 21 including controlling the pressure in said at least a portion of said first portion of said cleaning fluid withdrawn from said outlet side of said concentrate filter.

23. The method of claim 21 including controlling the pressure in said at least a portion of said first portion of said cleaning fluid withdrawn from said outlet side of said concentrate filter and controlling the pressure in said second portion of said cleaning fluid withdrawn from said inlet side of said concentrate filter.

24. The method of claim 23 including controlling said pressure of said at least a portion of said first portion of said cleaning fluid to a higher pressure than said second portion of said cleaning fluid.

25. The method of claim 16 including supplying water to the inlet side of a water filter, withdrawing said filtered water from the outlet side of said water filter, intermittently supplying cleaning fluid to said inlet side of said water filter so as to clean said water filter, withdrawing a first portion of said cleaning fluid from said outlet side of said water filter, and withdrawing a second portion of said cleaning fluid from said inlet side of said water filter, so as to simultaneously flush said inlet side and said outlet side of said water filter with said cleaning fluid during said cleaning of said water filter, supplying said filtered water withdrawn from said outlet side of said water filter to said primary supply conduit for said medical treatment process, and intermittently supplying at least a portion of said cleaning fluid withdrawn from said outlet side of said water filter to said inlet side of said concentrate filter so as to clean said concentrate filter.

* * * * *

UNITED STATES PATENT AND TRADEMARK OFFICE
CERTIFICATE OF CORRECTION

PATENT NO. : 4,783,273

DATED : November 8, 1988

INVENTOR(S) : Stefan L. Knutsson and Stanley Shaldon

It is certified that error appears in the above-identified patent and that said Letters Patent is hereby corrected as shown below:

Column 2, line 6, "not" should read --now--.
Column 2, line 34, "position" should read --portion--.
Column 6, line 56, cancel the word "of".
Column 8, line 50, "said", third occurrence, should read --side--.
Column 8, line 57, after "of" insert --said--.
Column 10, line 12, "filter" should read --fluid--.

Signed and Sealed this

Second Day of May, 1989

Attest:

DONALD J. QUIGG

*Attesting Officer*    *Commissioner of Patents and Trademarks*